US011307495B2

(12) United States Patent
Miyake et al.

(10) Patent No.: US 11,307,495 B2
(45) Date of Patent: Apr. 19, 2022

(54) THERMAL ACID GENERATOR AND RESIST COMPOSITION USING SAME

(71) Applicant: ADEKA CORPORATION, Tokyo (JP)

(72) Inventors: Junya Miyake, Tokyo (JP); Yoshitomo Takeuchi, Tokyo (JP); Naomi Sato, Tokyo (JP); Kentaro Kimura, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 167 days.

(21) Appl. No.: 16/071,397

(22) PCT Filed: Jan. 23, 2017

(86) PCT No.: PCT/JP2017/002106
§ 371 (c)(1),
(2) Date: Jul. 19, 2018

(87) PCT Pub. No.: WO2017/130896
PCT Pub. Date: Aug. 3, 2017

(65) Prior Publication Data

US 2020/0183271 A1 Jun. 11, 2020

(30) Foreign Application Priority Data

Jan. 26, 2016 (JP) ............................ JP2016-012814

(51) Int. Cl.
*G03F 7/004* (2006.01)
*C07D 221/14* (2006.01)

(52) U.S. Cl.
CPC ........... *G03F 7/004* (2013.01); *C07D 221/14* (2013.01)

(58) Field of Classification Search
CPC .............................. C03F 7/004; C07D 221/14
USPC ............................................................ 546/98
See application file for complete search history.

(56) References Cited

U.S. PATENT DOCUMENTS

| | | | |
|---|---|---|---|
| 7,638,262 | B2 | 12/2009 | Wu et al. |
| 8,349,533 | B2 | 1/2013 | Ohsawa et al. |
| 2002/0012880 | A1 | 1/2002 | Imai et al. |
| 2015/0315153 | A1 | 11/2015 | Yanagisawa et al. |
| 2016/0368879 | A1 | 12/2016 | Ikeda et al. |

FOREIGN PATENT DOCUMENTS

| | | | | | |
|---|---|---|---|---|---|
| JP | 2000-187326 | A | | 7/2000 | |
| JP | 2001-22057 | A | | 1/2001 | |
| JP | 2004-217748 | A | | 8/2004 | |
| JP | 2004217748 | A | * | 8/2004 | |
| JP | 2007-8919 | A | | 1/2007 | |
| JP | 4813537 | B2 | | 11/2011 | |
| JP | 5453615 | B2 | | 3/2014 | |
| JP | 2014/80524 | A | | 5/2014 | |
| JP | 2015-168618 | A | | 9/2015 | |
| JP | 5789461 | B2 | | 10/2015 | |
| WO | WO-20100029273 | A1 | * | 1/2010 | ............ C08G 73/00 |

(Continued)

OTHER PUBLICATIONS

International Search Report issued in PCT/JP2017/002106 (PCT/ISA/210), dated Mar. 7, 2017.

(Continued)

*Primary Examiner* — Timothy R Rozof

(74) *Attorney, Agent, or Firm* — Birch, Stewart, Kolasch & Birch, LLP

(57) ABSTRACT

Provided are: a thermal acid generator having a high acid generation temperature; and a resist composition using the same. The thermal acid generator is a sulfonic acid derivative compound represented by the following Formula (I): (wherein, $R^1$ represents an aliphatic hydrocarbon group having 1 to 18 carbon atoms or the like, or a group represented by the following Formula (II): (wherein, $Y^1$ represents a single bond or an alkanediyl group having 1 to 4 carbon atoms; $R^{11}$ and $R^{12}$ each independently represent an alkanediyl group having 2 to 6 carbon atoms, or the like; $R^{13}$ represents a linear or branched alkyl group having 1 to 18 carbon atoms, or the like; a and b each represent 0 or 1; and either a or b is 1); $R^2$ to $R^7$ each independently represent a linear or branched alkyl group having 1 to 14 carbon atoms; the aliphatic hydrocarbon group or the like of $R^1$ has no substituent or is substituted with a halogen atom or the like; and a methylene structure in the aliphatic hydrocarbon group or the like of $R^1$ is optionally substituted with —O— or the like).

(I)

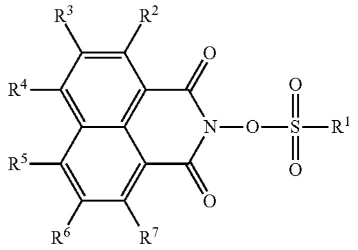

(II)

$$-R^{11}\!\left(O\right)_a R^{12}\!\left(O\right)_b Y^1-R^{13}$$

6 Claims, No Drawings

(56) References Cited

FOREIGN PATENT DOCUMENTS

| | | | | | |
|---|---|---|---|---|---|
| WO | WO-2011087011 | A1 * | 7/2011 | ........... | G03F 7/0046 |
| WO | WO 2014/084269 | A1 | 6/2014 | | |
| WO | WO-2014084269 | A1 * | 6/2014 | ............. | G03F 7/038 |
| WO | WO 2015/001804 | A1 | 1/2015 | | |
| WO | WO-2015001804 | A1 * | 1/2015 | ............. | G03F 7/039 |

OTHER PUBLICATIONS

Written Opinion of the International Searching Authority issued in PCT/JP2017/002106 (PCT/ISA/237), dated Mar. 7, 2017.

* cited by examiner

THERMAL ACID GENERATOR AND RESIST COMPOSITION USING SAME

TECHNICAL FIELD

The present invention relates to a thermal acid generator, and a resist composition comprising the same. More particularly, the present invention relates to a thermal acid generator having a high acid generation temperature, and a resist composition comprising the same.

BACKGROUND ART

Thermal acid generators are used in a variety of applications, such as semiconductors, display elements, sealants, and overcoating agent. Various reports have been made with regard to such thermal acid generators.

For example, Patent Document 1 discloses a thermal acid generator composed of a sulfonium salt. In addition, Patent Documents 2 to 4 disclose thermal acid generator-containing resist materials. Further, Patent Document 4 discloses that an onium salt-based thermal acid generator has a thermal acid generation temperature of 100° C. or higher. Still further, Patent Document 5 discloses a photoacid generator composed of a sulfonic acid derivative compound having a specific structure.

RELATED ART DOCUMENTS

Patent Documents

[Patent Document 1] Japanese Unexamined Patent Application Publication No. 2007-008919

[Patent Document 2] Japanese Patent No. 5453615

[Patent Document 3] Japanese Patent No. 5789461

[Patent Document 4] Japanese Patent No. 4813537

[Patent Document 5] WO2014/084269

SUMMARY OF THE INVENTION

Problems to be Solved by the Invention

However, Patent Document 5 offers no disclosure or suggestion that a sulfonic acid derivative compound can be used as a thermal acid generator. Thus, there is still room for investigation with regard to the structure of a thermal acid generator having a high acid generation temperature. In view of this, an object of the present invention is to provide: a thermal acid generator having a high acid generation temperature; and a resist composition comprising the same.

Means for Solving the Problems

The present inventors intensively studied to solve the above-described problem and consequently discovered that a sulfonic acid derivative compound having a specific structure can solve the above-described problem, thereby completing the present invention.

That is, the thermal acid generator of the present invention is characterized by being represented by the following Formula (I):

(I)

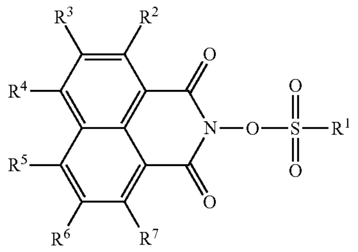

(wherein, $R^1$ represents an aliphatic hydrocarbon group having 1 to 18 carbon atoms, an aryl group having 6 to 20 carbon atoms, an arylalkyl group having 7 to 20 carbon atoms, an acyl group-substituted aryl group having 7 to 20 carbon atoms, an alicyclic hydrocarbon group having 3 to 12 carbon atoms, a 10-camphoryl group, or a group represented by the following Formula (II):

$$—R^{11}—(O)_a—R^{12}—(O)_b—Y^1—R^{13} \quad (II)$$

(wherein, $Y^1$ represents a single bond or an alkanediyl group having 1 to 4 carbon atoms; $R^{11}$ and $R^{12}$ each independently represent an alkanediyl group having 2 to 6 carbon atoms, a halogenated alkanediyl group having 2 to 6 carbon atoms, an arylene group having 6 to 20 carbon atoms, or a halogenated arylene group having 6 to 20 carbon atoms; $R^{13}$ represents a linear or branched alkyl group having 1 to 18 carbon atoms, a linear or branched halogenated alkyl group having 1 to 18 carbon atoms, an alicyclic hydrocarbon group having 3 to 12 carbon atoms, an aryl group having 6 to 20 carbon atoms, a halogenated aryl group having 6 to 20 carbon atoms, an arylalkyl group having 7 to 20 carbon atoms, or a halogenated arylalkyl group having 7 to 20 carbon atoms; a and b each represent 0 or 1; and either a or b is 1);

$R^2$, $R^3$, $R^4$, $R^5$, $R^6$ and $R^7$ each independently represent a linear or branched alkyl group having 1 to 14 carbon atoms, or a silyl group;

the aliphatic hydrocarbon group, aryl group, arylalkyl group or alicyclic hydrocarbon group of $R^1$ has no substituent, or is substituted with a halogen atom or a group selected from a halogenated alkyl group having 1 to 4 carbon atoms, an alkoxy group having 1 to 18 carbon atoms and an alkylthio group having 1 to 18 carbon atoms; and a methylene structure in the aliphatic hydrocarbon group, arylalkyl group or alicyclic hydrocarbon group of $R^1$ is optionally substituted with —O—, —S—, —SO—, —$SO_2$—, —CO—, —COO—, —OCO—, —OCOO—, —NHCO—, or —CONH—).

In the thermal acid generator of the present invention, it is preferred that $R^4$ be an alkyl group having 4 carbon atoms. In the thermal acid generator of the present invention, it is also preferred that $R^1$ be a perfluoroalkyl group having 1 to 8 carbon atoms.

The resist composition of the present invention is characterized by comprising the thermal acid generator of the present invention.

Effects of the Invention

According to the present invention, a thermal acid generator having a high acid generation temperature, and a resist composition comprising the same can be provided.

MODE FOR CARRYING OUT THE INVENTION

The present invention will now be described in detail based on embodiments thereof.

First, the sulfonic acid derivative compound represented by the Formula (1) will be described. The thermal acid generator of the present invention is composed of a sulfonic acid derivative compound represented by the following Formula (I):

(I)

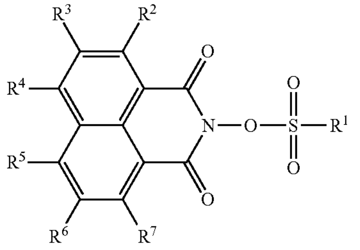

In the Formula (I), $R^1$ represents an aliphatic hydrocarbon group having 1 to 18 carbon atoms, an aryl group having 6 to 20 carbon atoms, an arylalkyl group having 7 to 20 carbon atoms, an acyl group-substituted aryl group having 7 to 20 carbon atoms, an alicyclic hydrocarbon group having 3 to 12 carbon atoms, a 10-camphoryl group, or a group represented by the following Formula (II), and the aliphatic hydrocarbon group, aryl group, arylalkyl group or alicyclic hydrocarbon group has no substituent, or is optionally substituted with a halogen atom or a group selected from a halogenated alkyl group having 1 to 4 carbon atoms, an alkoxy group having 1 to 18 carbon atoms and an alkylthio group having 1 to 18 carbon atoms. Further, a methylene structure in the aliphatic hydrocarbon group, arylalkyl group or alicyclic hydrocarbon group of $R^1$ is optionally substituted with —O—, —S—, —SO—, —$SO_2$—, —CO—, —COO—, —OCO—, —OCOO—, —NHCO—, or —CONH—.

$$—R^{11}—(O)_a—R^{12}—(O)_b—Y^1—R^{13} \quad (II)$$

In the Formula (II), $Y^1$ represents a single bond or an alkanediyl group having 1 to 4 carbon atoms; $R^{11}$ and $R^{12}$ each independently represent an alkanediyl group having 2 to 6 carbon atoms, a halogenated alkanediyl group having 2 to 6 carbon atoms, an arylene group having 6 to 20 carbon atoms, or a halogenated arylene group having 6 to 20 carbon atoms; $R^{13}$ represents a linear or branched alkyl group having 1 to 18 carbon atoms, a linear or branched halogenated alkyl group having 1 to 18 carbon atoms, an alicyclic hydrocarbon group having 3 to 12 carbon atoms, an aryl group having 6 to 20 carbon atoms, a halogenated aryl group having 6 to 20 carbon atoms, an arylalkyl group having 7 to 20 carbon atoms, or a halogenated arylalkyl group having 7 to 20 carbon atoms; a and b each represent 0 or 1; and either a or b is 1.

In the Formula (I), $R^1$ represents an aliphatic hydrocarbon group having 1 to 18 carbon atoms, an aryl group having 6 to 20 carbon atoms, an arylalkyl group having 7 to 20 carbon atoms, an acyl group-substituted aryl group having 7 to 20 carbon atoms, an alicyclic hydrocarbon group having 3 to 12 carbon atoms, a 10-camphoryl group, or a group represented by the Formula (II). Among these groups, the aliphatic hydrocarbon group, the aryl groups and the arylalkyl group optionally do not have any substituent, or are optionally substituted with a halogen atom or a group selected from a halogenated alkyl group having 1 to 4 carbon atoms, an alkoxy group having 1 to 18 carbon atoms and an alkylthio group having 1 to 18 carbon atoms.

Examples of the halogen atom as a substituent include chlorine, bromine, iodine, and fluorine. Examples of the halogenated alkyl group include a trifluoromethyl group.

Examples of the alkoxy group having 1 to 18 carbon atoms as a substituent include methoxy, ethoxy, propoxyl, butoxy, tert-butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, and octadecyloxy.

Examples of the alkylthio group having 1 to 18 carbon atoms as a substituent include methylthio, ethylthio, propylthio, isopropylthio, butylthio, sec-butylthio, tert-butylthio, isobutylthio, amylthio, isoamylthio, tert-amylthio, hexylthio, heptylthio, isoheptylthio, tert-heptylthio, octylthio, isooctylthio, tert-octylthio, 2-ethylhexylthio, nonylthio, decylthio, undecylthio, dodecylthio, tridecylthio, tetradecylthio, pentadecylthio, hexadecylthio, heptadecylthio, and octadecylthio.

Examples of the aliphatic hydrocarbon group having 1 to 18 carbon atoms that is represented by $R^1$ include an alkenyl group, an alkyl group, a group in which a methylene group in an alkyl group is substituted with an alicyclic hydrocarbon group, a group in which a proton of a methylene group in an alkyl group is substituted with an alicyclic hydrocarbon group, and a group in which an alicyclic hydrocarbon exists at a terminal of an alkyl group. Examples of the alkenyl group include allyl and 2-methyl-2-propenyl, and examples of the alkyl group include methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, and octadecyl. Examples of the alicyclic hydrocarbon group include, stating them in terms of the names of cycloalkanes constituting the respective alicyclic hydrocarbon groups: cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane.

Examples of the aliphatic hydrocarbon group having 1 to 18 carbon atoms that is represented by $R^1$ and substituted with a halogen atom include halogenated alkyl groups, such as trifluoromethyl, pentafluoroethyl, 2-chloroethyl, 2-bromoethyl, heptafluoropropyl, 3-bromopropyl, nonafluorobutyl, tridecafluorohexyl, heptadecafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, norbornyl-1,1-difluoroethyl, norbornyltetrafluoroethyl, adamantane-1,1,2,2-tetrafluoropropyl, and bicyclo[2.2.1]heptane-tetrafluoromethyl.

Examples of the aliphatic hydrocarbon group having 1 to 18 carbon atoms that is represented by $R^1$ and substituted with an alkylthio group having 1 to 18 carbon atoms include 2-methylthioethyl, 4-methylthiobutyl and 4-butylthioethyl, and examples of the aliphatic hydrocarbon having 1 to 18 carbon atoms which is substituted with both a halogen atom and an alkylthio group having 1 to 18 carbon atoms include 1,1,2,2-tetrafluoro-3-methylthiopropyl.

Examples of the aryl group having 6 to 20 carbon atoms that is represented by $R^1$ include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, cyclohexylphenyl, biphenyl, 2,4,5-trimethylphenyl, 2,4,6-trimethylphenyl, and 2,4,6-triisopropylphenyl.

Examples of the aryl group having 6 to 20 carbon atoms that is represented by $R^1$ and substituted with a halogen atom include pentafluorophenyl, chlorophenyl, dichlorophenyl, trichlorophenyl, 2,4-bis(trifluoromethyl)phenyl, and bromoethylphenyl.

Examples of the aryl group having 6 to 20 carbon atoms that is represented by $R^1$ and substituted with an alkylthio group having 1 to 18 carbon atoms include 4-methylthiophenyl, 4-butylthiophenyl, 4-octylthiophenyl, and 4-dodecylthiophenyl. Examples of the aryl group having 6 to 20 carbon atoms that is represented by $R^1$ and substituted with a halogen atom and an alkylthio group having 1 to 18 carbon atoms include 1,2,5,6-tetrafluoro-4-methylthiophenyl, 1,2,5,6-tetrafluoro-4-butylthiophenyl, and 1,2,5,6-tetrafluoro-4-dodecylthiophenyl.

Examples of the arylalkyl group having 7 to 20 carbon atoms that is represented by $R^1$ include benzyl, phenethyl, 2-phenylpropan-2-yl, diphenylmethyl, triphenylmethyl, styryl, and cinnamyl.

Examples of the arylalkyl group that is represented by $R^1$ and substituted with a halogen atom include pentafluorophenylmethyl, phenyldifluoromethyl, 2-phenyl-tetrafluoroethyl, and 2-(pentafluorophenyl)ethyl. Examples of the arylalkyl group having 7 to 20 carbon atoms that is substituted with an alkylthio group having 1 to 18 carbon atoms include p-methylthiobenzyl. Examples of the arylalkyl group that is substituted with a halogen atom and an alkylthio group having 1 to 18 carbon atoms include 2,3,5,6-tetrafluoro-4-methylthiophenylethyl.

The number of carbon atoms of the acyl group-substituted aryl group having 7 to 20 carbon atoms which is represented by $R^1$ includes the carbon atoms of the acyl group. Examples of such an aryl group include acetylphenyl, acetylnaphthyl, benzoylphenyl, 1-anthraquinolyl, and 2-anthraquinolyl.

Examples of the alicyclic hydrocarbon group having 3 to 12 carbon atoms that is represented by $R^1$ include, stating them in terms of the names of cycloalkanes constituting the respective alicyclic hydrocarbon groups: cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane.

The Formula (II) is an ether group. In the Formula (II), examples of the alkanediyl group having 1 to 4 carbon atoms which is represented by $Y^1$ include methylene, ethylene, propane-1,3-diyl, propane-1,2-diyl, butylene, butane-1,3-diyl, butane-2,3-diyl, and butane-1,2-diyl.

Examples of the alkanediyl group having 2 to 6 carbon atoms that is represented by $R^{11}$ and/or $R^{12}$ include ethylene, propane-1,3-diyl, propane-1,2-diyl, butylene, butane-1,3-diyl, butane-2,3-diyl, butane-1,2-diyl, pentane-1,5-diyl, pentane-1,3-diyl, pentane-1,4-diyl, pentane-2,3-diyl, hexane-1,6-diyl, hexane-1,2-diyl, hexane-1,3-diyl, hexane-1,4-diyl, hexane-2,5-diyl, hexane-2,4-diyl, and hexane-3,4-diyl.

Examples of the halogenated alkanediyl group having 2 to 6 carbon atoms that is represented by $R^{11}$ and/or $R^{12}$ include the above-described alkanediyl groups having 2 to 6 carbon atoms in which at least one proton is substituted with a halogen atom. Examples of the halogen atom include chlorine, bromine, iodine, and fluorine. Examples of such halogenated alkanediyl group having 2 to 6 carbon atoms include tetrafluoroethylene, 1,1-difluoroethylene, 1-fluoroethylene, 1,2-difluoroethylene, hexafluoropropane-1,3-diyl, 1,1,2,2-tetrafluoropropane-1,3-diyl, and 1,1,2,2-tetrafluoropentane-1,5-diyl.

Examples of the arylene group having 6 to 20 carbon atoms that is represented by $R^{11}$ and/or $R^{12}$ include 1,2-phenylene, 1,3-phenylene, 1,4-phenylene, 2,5-dimethyl-1,4-phenylene, 4,4'-biphenylene, diphenylmethane-4,4'-diyl, 2,2-diphenylpropane-4,4'-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, and naphthalene-2,7-diyl.

Examples of the halogenated arylene group having 6 to 20 carbon atoms that is represented by $R^{11}$ and/or $R^{12}$ include the above-described arylene groups having 6 to 20 carbon atoms in which at least one proton is substituted with a halogen atom. Examples of the halogen atom include chlorine, bromine, iodine, and fluorine. Examples of such halogenated arylene group having 6 to 20 carbon atoms include tetrafluorophenylene.

Examples of the alkyl group having 1 to 18 carbon atoms that is represented by $R^{13}$ include methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, and octadecyl.

Examples of the halogenated alkyl group having 1 to 18 carbon atoms that is represented by $R^{13}$ include the alkyl groups having 1 to 18 carbon atoms in which at least one proton is substituted with a halogen atom. Examples of the halogen atom include chlorine, bromine, iodine, and fluorine. Examples of such halogenated alkyl group having 1 to 18 carbon atoms include halogenated alkyl groups, such as trifluoromethyl, pentafluoroethyl, heptafluoropropyl, nonafluorobutyl, tridecafluorohexyl, heptadecafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, and 1,1,2,2-tetrafluorotetradecyl.

Examples of the alicyclic hydrocarbon group having 3 to 12 carbon atoms that is represented by $R^{13}$ include, stating them in terms of the names of cycloalkanes constituting the respective alicyclic hydrocarbon groups: cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane.

Examples of the aryl group having 6 to 20 carbon atoms, halogenated aryl group having 6 to 20 carbon atoms, arylalkyl group having 7 to 20 carbon atoms or halogenated arylalkyl group having 7 to 20 carbon atoms that is represented by $R^{13}$ include the same groups as those exemplified above for $R^1$.

A group preferred as the Formula (II) is a group having a total of 2 to 18 carbon atoms in which fluorine is bound to a carbon atom of a group represented by $R^{11}$ that is adjacent to a sulfur atom since such a group has good acid generation capacity, cationic polymerizability and the like.

In the Formula (I), $R^2$, $R^3$, $R^4$, $R^5$, $R^6$ and $R^7$ each independently represent a linear or branched alkyl group having 1 to 14 carbon atoms, or a silyl group.

Examples of the linear or branched alkyl group having 1 to 14 carbon atoms include methyl, ethyl, propyl, isopropyl, 1-butyl, 2-butyl, isobutyl, tert-butyl, 1-pentyl, isopentyl, tert-pentyl, neopentyl, 1-hexyl, 2-hexyl, 3-hexyl, heptyl, 2-heptyl, 3-heptyl, isoheptyl, tert-heptyl, 1-octyl, isooctyl, tert-octyl, 2-ethylhexyl, 1-nonyl, isononyl, 1-decyl, and 1-dodecyl. Thereamong, an alkyl group having 3 to 8 carbon atoms is preferred and an alkyl group having 4 carbon atoms is more preferred since these alkyl groups have both good solubility and good acid generation rate. A 1-butyl group is still more preferred since it makes the material inexpensive and has a good yield and a low production cost. Further, the alkyl group is preferably an unsubstituted alkyl group.

Examples of the silyl group a trimethylsilyl group, an ethyldimethylsilyl group, a methyldiethylsilyl group, a triethylsilyl group, an isopropyldimethylsilyl group, a methyldiisopropylsilyl group, a triisopropylsilyl group, a t-butyldimethylsilyl group, a methyl-di-t-butylsilyl group, a tri-t-butylsilyl group, a phenyldimethylsilyl group, a methyldiphenylsilyl group, and a triphenylsilyl group.

The compound according to the thermal acid generator of the present invention is preferably a compound which has a linear or branched alkyl group having 1 to 14 carbon atoms at a specific position of a naphthalimide skeleton of a photosensitive group, that is, at 4-position of a naphthalene structure.

Specific examples of the sulfonic acid derivative compound represented by the Formula (I) include the following Compound Nos. 1 to 58.

Compound No.1

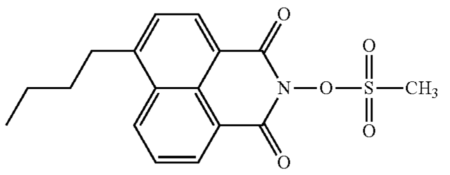

Compound No.2

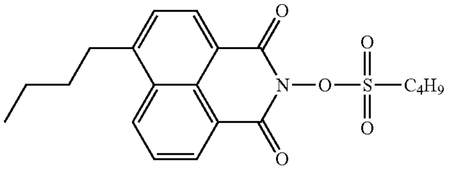

Compound No.3

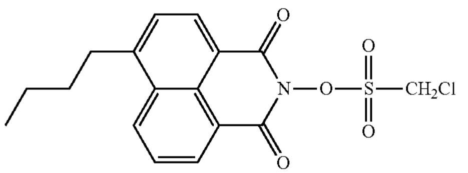

-continued

Compound No.4

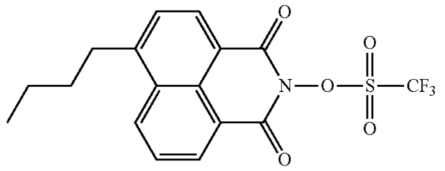

Compound No.5

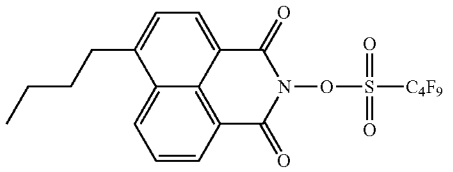

Compound No.6

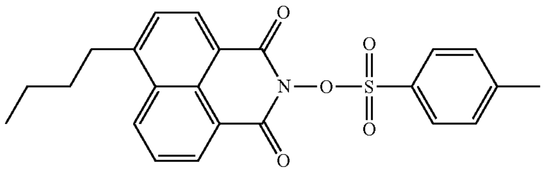

Compound No.7

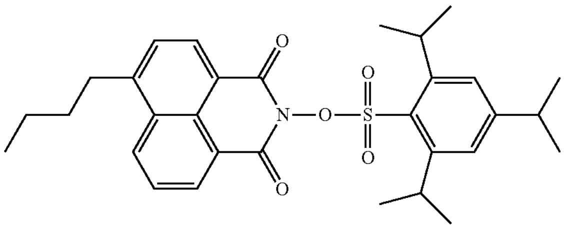

Compound No.8

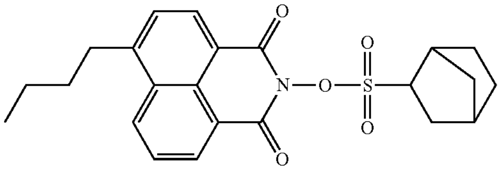

Compound No.9

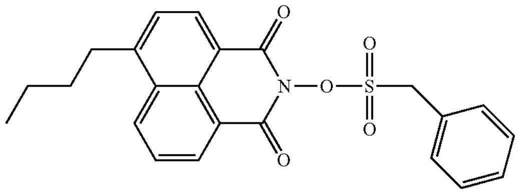

Compound No.10

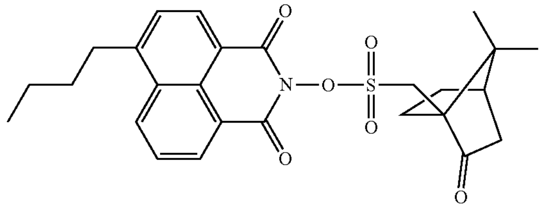

-continued
Compound No.11
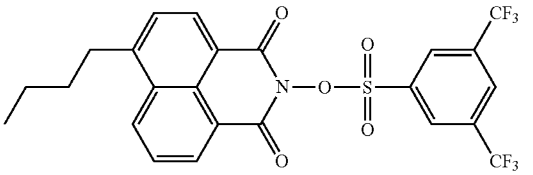
Compound No.12
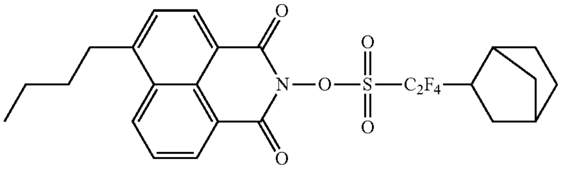
Compound No.13
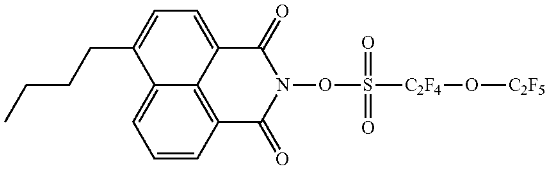
Compound No.14
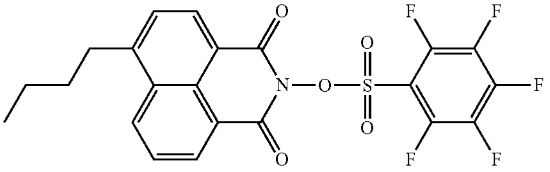
Compound No.15
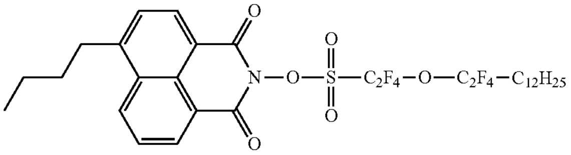
Compound No.16
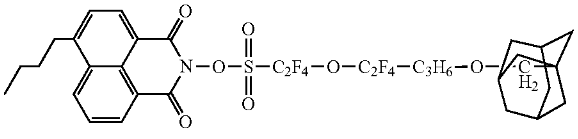
Compound No.17
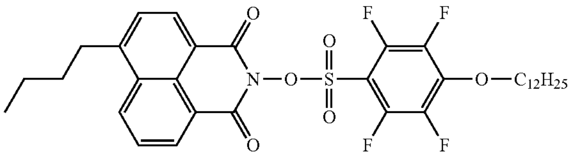
Compound No.18
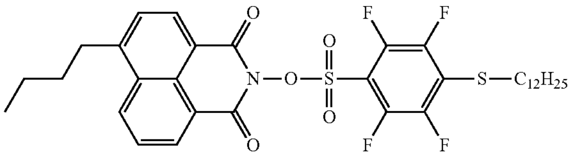
-continued
Compound No.19
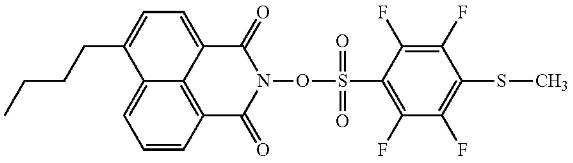
Compound No.20
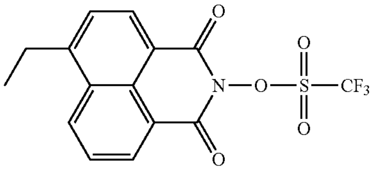
Compound No.21
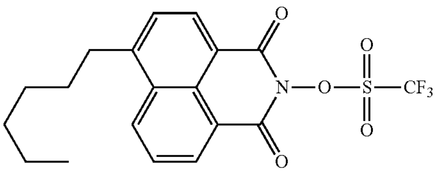
Compound No.22
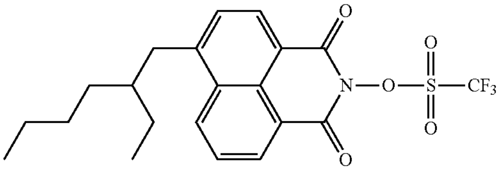
Compound No.23
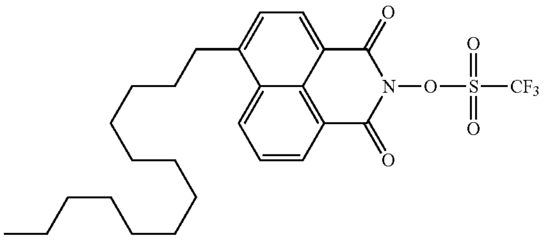
Compound No.24
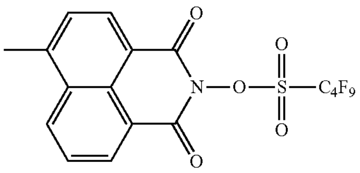
Compound No.25
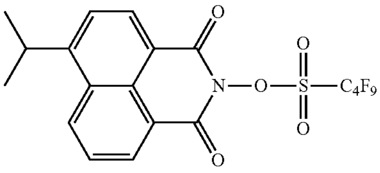

-continued
Compound No.26
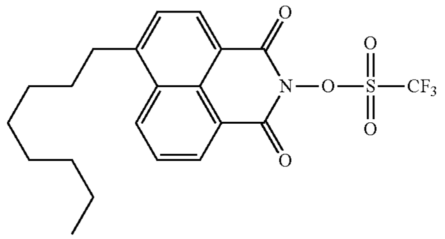
Compound No.27
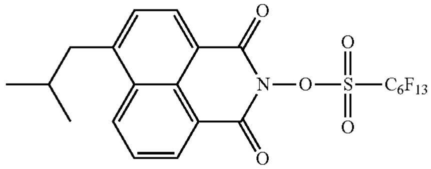
Compound No.28
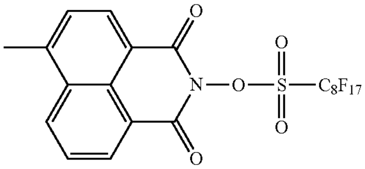
Compound No.29
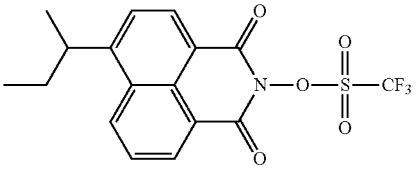
Compound No.30
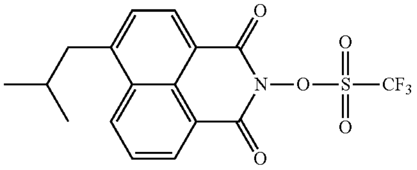
Compound No.31
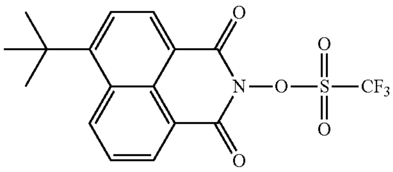
Compound No.32
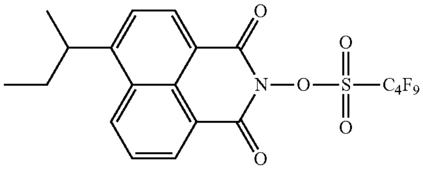
-continued
Compound No.33
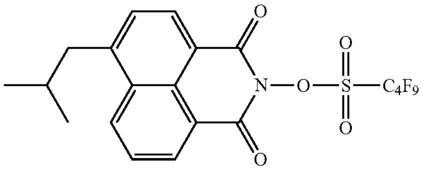
Compound No.34
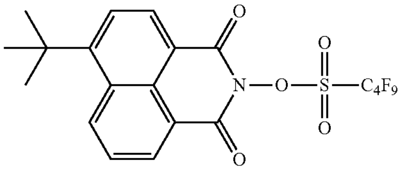
Compound No.35
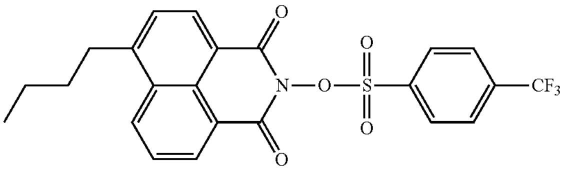
Compound No.36
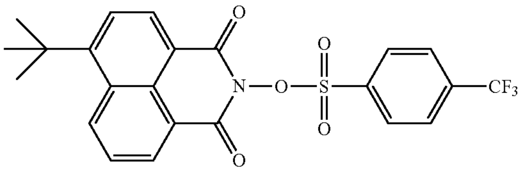
Compound No.37
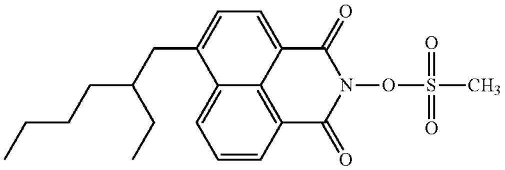
Compound No.38
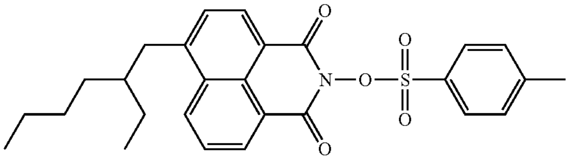
Compound No.39
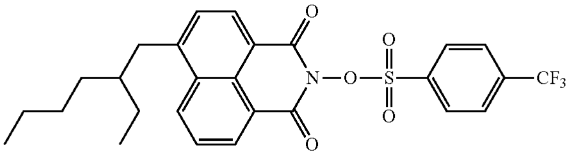
Compound No.40
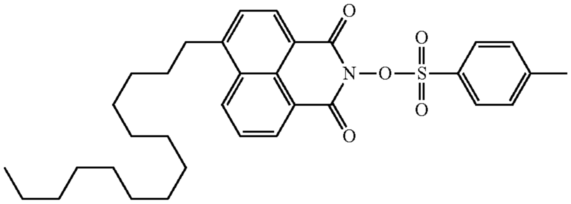

-continued
Compound No.41
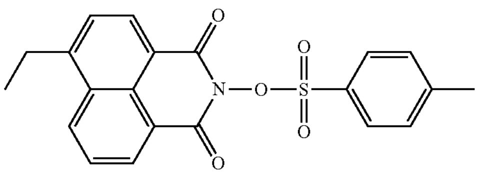
Compound No.42
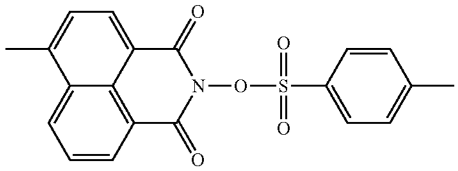
Compound No.43
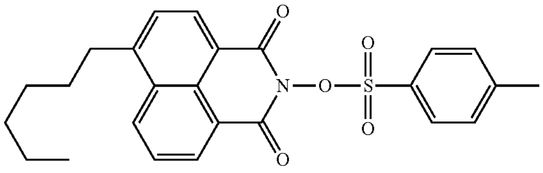
Compound No.44
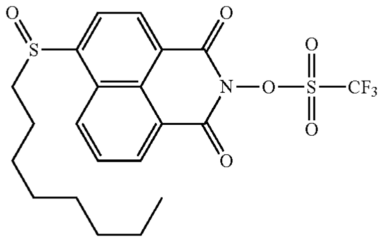
Compound No.45
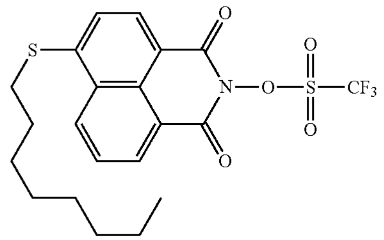
Compound No.46
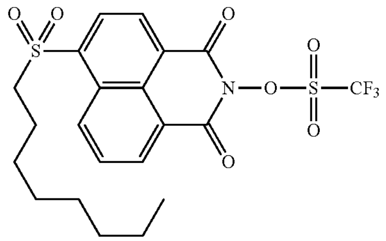
Compound No.47
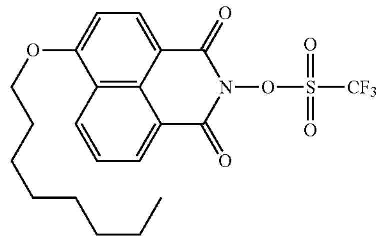
-continued
Compound No.48
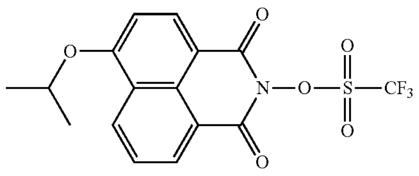
Compound No.49
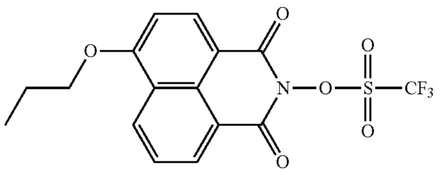
Compound No.50
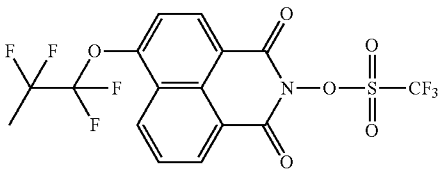
Compound No.51
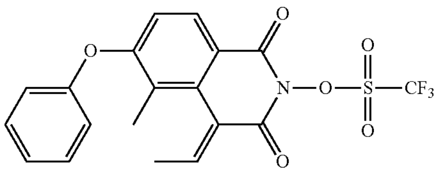
Compound No.52
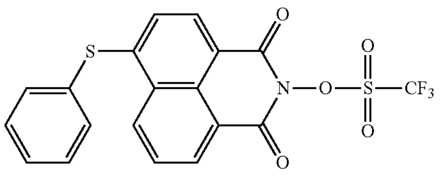
Compound No.53
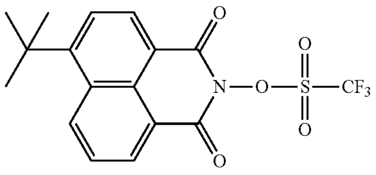
Compound No.54
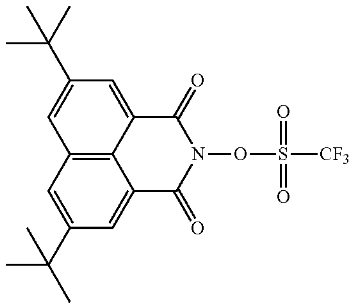

-continued

Compound No.55

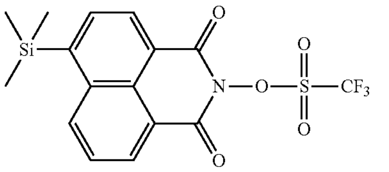

Compound No.56

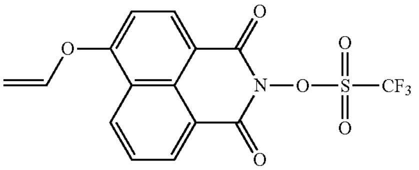

Compound No.57

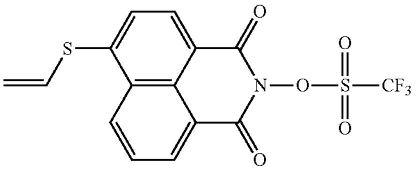

Compound No.58

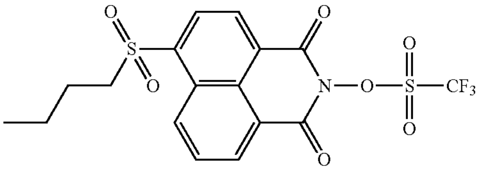

In the Formula (I), $R^1$ may be selected such that the sulfonic acid derivative compound releases an organic sulfonic acid appropriate for the intended use; however, $R^1$ is preferably a perfluoroalkyl group having 1 to 8 carbon atoms since a high acid strength is attained.

The method of producing the sulfonic acid derivative compound represented by the Formula (I) is not particularly restricted, and a well-known chemical reaction can be applied to synthesize the sulfonic acid derivative compound. For example, a method of synthesizing a sulfonic acid derivative compound using a bromide as a starting substance in the below described manner can be employed.

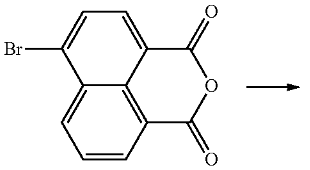

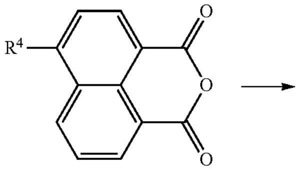

-continued

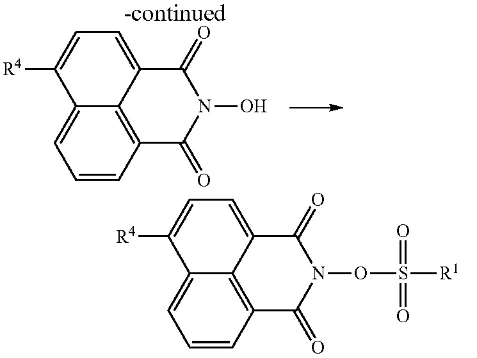

(wherein, $R^1$ and $R^4$ each represent the same group as in the Formula (I))

The thermal acid generator of the present invention has a property of releasing a Lewis acid when heated, and is capable of acting on an acid-reactive organic substance to induce decomposition or polymerization thereof. The heating conditions are: at 70 to 300° C., preferably 200 to 250° C., for 1 to 100 minutes. After pre-baking, the resultant may be post-baked under pressure, or baking may be performed at different temperatures in several stages.

In cases where the thermal acid generator of the present invention is used for an acid-reactive organic substance, the amount thereof is not particularly restricted; however, it is preferably 0.05 to 100 parts by mass, more preferably 0.05 to 20 parts by mass, with respect to 100 parts by mass of the acid-reactive organic substance. It is noted here that the thermal acid generator of the present invention may be used in an amount that is greater or less than the above-described range, depending on the factors such as the properties of the acid-reactive organic substance, the light irradiation intensity, the time required for reaction, the physical properties, and the cost.

The acid-reactive organic substance is polymerized or cross-linked by an acid generated from the thermal acid generator when heated, and a variety of monomers, oligomers and polymers that have a cationically polymerizable functional group, such as a vinyl ether group, an epoxy group, an alicyclic epoxy group, an oxetanyl group, an episulfide group, an ethylene imine group or a hydroxyl group, can be used. Further, the polymers having such a functional group are also not restricted, and a variety of polymers, such as acrylic polymers, urethane-based polymers, polyester-based polymers, polyolefin-based polymers, polyether-based polymers, natural rubbers, block copolymer rubbers and silicone-based polymers, can be used.

Specific examples of the acid-reactive organic substance include epoxy compounds, styrenes, vinyl compounds, vinyl ethers, oxetane compounds, spiro-orthoesters, bicyclo-orthoesters, spiro-orthocarbonates, cyclic ethers, lactones, oxazolines, aziridines, cyclosiloxanes, ketals, cyclic acid anhydrides, lactams, and aryldialdehydes, as well as polymerizable or cross-linkable polymers and oligomers that have any of these polymerizable groups in a side chain. These acid-reactive organic substances may be used individually, or in combination of two or more thereof.

Examples of the epoxy compounds include aromatic epoxy resins, such as bisphenol A-type epoxy resins, glycidyl ether-type epoxy resins, phenol novolac-type epoxy resins, bisphenol F-type epoxy resins, bisphenol S-type epoxy resins, cresol novolac-type epoxy resins, glycidylamine-type epoxy resins, naphthalene-type epoxy resins, polyfunctional epoxy resins, biphenyl-type epoxy resins, glycidyl ester-type epoxy resins, and hydrogenated bisphenol A-type epoxy resin; aliphatic epoxy resins, such as 1,4-butanediol diglycidyl ether, 1,6-hexanediol diglycidyl ether, ethylene glycol diglycidyl ether, ethylene glycol monoglycidyl ether, propylene glycol diglycidyl ether, propylene glycol monoglycidyl ether, polyethylene glycol diglycidyl ether, propylene glycol diglycidyl ether, neopentyl glycol diglycidyl ether, neopentyl glycol monoglycidyl ether, glycerol diglycidyl ether, glycerol triglycidyl ether, trimethylolpropane diglycidyl ether, trimethylolpropane monoglycidyl ether, trimethylolpropane triglycidyl ether, diglycerol triglycidyl ether, sorbitol tetraglycidyl ether, allyl glycidyl ether, and 2-ethylhexylglycidyl ether; alicyclic epoxy resins, such as 1,2:8,9-diepoxy limonene, 4-vinylcyclohexene monoepoxide, vinylcyclohexene dioxide, methylated vinylcyclohexene dioxide, (3,4-epoxycyclohexyl) methyl-3,4-epoxycyclohexyl carboxylate, bis-(3,4-epoxycyclohexyl)adipate, norbornene monoepoxide, limonene monoepoxide, 2-(3,4-epoxycyclohexyl-5,5-spiro-3,4-epoxy)cyclohexanone-meth-dioxane, bis-(3,4-epoxycyclohexylmethylene)adipate, bis-(2,3-epoxycyclopentyl) ether, (2,3-epoxy-6-methylcyclohexylmethyl)adipate, dicyclopentadiene dioxide, 2-(3,4-epoxycyclohexyl-5,5-spiro-3,4-epoxy)cyclohexane-meth-dioxane, and 2,2-bis[4-(2,3-epoxypropoxy)cyclohexyl]hexafluoropropane; halogenated epoxy resins such as brominated epoxy resins; rubber-modified epoxy resins; urethane-modified epoxy resins; epoxidized polybutadienes; epoxidized styrene-butadiene-styrene block copolymers; epoxy-modified polyester resins; epoxy-modified polyurethane resins; and epoxy-modified acrylic resins. Further, epoxy group-containing oligomers and addition polymers of the above-described epoxy group-containing monomers or oligomers can also be used.

Examples of the oxetane compounds include phenoxymethyl oxetane, 3,3-bis(methoxymethyl)oxetane, 3,3-bis(phenoxymethyl)oxetane, 3-ethyl-3-(phenoxymethyl)oxetane, 3-ethyl-3-(2-ethylhexyloxymethyl)oxetane, 3-ethyl-3-{[3-(triethoxysilyl)propoxy]methyl}oxetane, di[1-ethyl(3-oxetanyl)]methyl ether, oxetanyl silsesquioxane, phenol novolac oxetane, and 1,4-bis{[(3-ethyl-3-oxetanyl) methoxy]methyl}benzene.

In positive-type photoresists, a resin which is changed toward having an increased solubility in a developing solution through, for example, cleavage of a chemical bond of an ester group, an acetal group or the like that is caused by the action of an acid (hereinafter, such a resin is also referred to as “resist base resin”) is used, whereas in negative-type photoresists, a compound or resin which is changed to have a reduced solubility in a developing solution due to the formation of a chemical bond through polymerization, cross-linking or the like that is caused by the action of an acid is used.

Examples of the resist base resin or compound include polyhydroxystyrenes and derivatives thereof; polyacrylic acids and derivatives thereof; polymethacrylic acids and derivatives thereof; copolymers formed by two or more selected from hydroxystyrene, acrylic acid, methacrylic acid and derivatives thereof; copolymers formed by two or more selected from hydroxystyrene, styrene and derivatives thereof; copolymers formed by three or more selected from cycloolefins and derivatives thereof, maleic anhydride, and acrylic acid and derivatives thereof; copolymers formed by three or more selected from cycloolefins and derivatives thereof, maleimide, and acrylic acid and derivatives thereof; polynorbornenes; high-molecular-weight polymers of one or more selected from the group consisting of metathesis ring-opening polymers; and these high-molecular-weight polymers which are partially substituted with an acid-labile group having an alkali dissolution-controlling ability. Examples of the acid-labile group incorporated into the high-molecular-weight polymers include tertiary alkyl groups, trialkylsilyl groups, oxoalkyl groups, aryl group-substituted alkyl groups, heteroalicyclic groups such as a tetrahydropyran-2-yl group, tertiary alkylcarbonyl groups, tertiary alkylcarbonylalkyl groups, and alkyloxycarbonyl groups.

Detailed specific examples of the resist base resin or compound are disclosed in, for example, Japanese Unexamined Patent Application Publication No. 2003-192665, claim 3 of Japanese Unexamined Patent Application Publication No. 2004-323704, and Japanese Unexamined Patent Application Publication No. H10-10733.

The polystyrene-equivalent weight-average molecular weight (Mw) of the resist base resin, which is determined by gel permeation chromatography (GPC), is usually 1,500 to 300,000, preferably 2,000 to 200,000, more preferably 3,000 to 100,000. In this case, when the Mw of the resist base resin is less than 1,500, the heat resistance as a resist tends to be reduced, whereas when the Mw is higher than 300,000, the developability and the coatability as a resist tend to be deteriorated.

The resist composition of the present invention is, prior to its use, normally adjusted by being dissolved in a solvent to a total solid concentration of usually 5 to 50% by mass, preferably 10 to 25% by mass, and subsequently filtered through, for example, a filter having a pore size of about 0.2 μm. The resist composition of the present invention can be prepared by a method of, for example, mixing, dissolving or kneading a thermal acid generator other than the thermal acid generator of the present invention, a photoacid generator, a resist base resin, and other arbitrary component(s).

The resist composition of the present invention is particularly useful as a chemically amplified resist. There are two types of chemically amplified resists depending on the action of an acid generated from a photoacid generator upon exposure: negative resists which undergo a chemical chain reaction and are made insoluble in a developing solution by a cross-linking reaction or polarity change of a base resin; and positive resists which are made soluble in a developing solution through a polarity change induced by a deprotection reaction of a high-molecular-weight side chain.

As a light source for exposure of the above-described resist composition, a variety of radiations, such as far-ultraviolet rays (e.g., ArF excimer laser (wavelength: 193 nm) and KrF excimer laser (wavelength: 248 nm)), X-rays (e.g., synchrotron radiation) and charged particle beams (e.g., electron beam and EUV), can be used.

Further, in the resist composition of the present invention, arbitrary additives can be used. Examples of such additives include organic solvents; benzotriazole-based, triazine-based, and benzoate-based ultraviolet absorbers; phenolic, phosphorus-based, and sulfur-based antioxidants; antistatic agents, such as cationic surfactants, anionic surfactants, nonionic surfactants, and amphoteric surfactants; flame retardants such as halogen-containing compounds, phosphate compounds, phosphoric amide compounds, melamine compounds, fluorocarbon resins, metal oxides, melamine (poly)phosphate, and piperazine (poly)phosphate; hydrocarbon-based, fatty acid-based, aliphatic alcohol-based, aliphatic ester-based, aliphatic amide-based, and metal soap-based lubricants; coloring agents such as dyes, pigments, and carbon blacks; silicate-based inorganic additives such as fumed silica, microparticulate silica, silica rock, diatomaceous earth, clay, kaolin, diatomaceous earth, silica gel, calcium silicate, sericite, kaolinite, flint, feldspar powder, vermiculite, attapulgite, talc, mica, minnesotaite, pyrophyllite, and silica; fillers, such as glass fibers and calcium carbonate; crystallization agents, such as nucleating agents and crystallization-promoting agents; silane coupling agents; rubber elasticity-imparting agents such as flexible polymers; and sensitizers. In the cationically polymerizable composition of the present invention, these additives are used in a total amount of 50% by mass or less.

Specific examples of the application of the resist composition of the present invention include, but not particularly limited to: optical filters; paints; coating agents; lining agents; adhesives; printing plates; insulating varnishes; insulation sheets; laminated plates; printed circuit boards; sealants for semiconductor devices, LED packages, liquid crystal inlets, organic EL devices, optical elements, electrical insulating materials, electronic components, separation membranes and the like; molded materials; putties; glass fiber impregnants; fillers; passivation films for semiconductors, solar cells and the like; interlayer insulation films and surface protection films that are used in thin-film transistors (TFT), liquid crystal displays, organic EL displays, printed boards and the like; color filters of printed boards, color televisions, PC monitors, personal digital assistants and CCD image sensors; electrode materials for plasma display panels; printing inks; dental compositions; resins for stereolithography; liquid-form films and dry films; micromachine components; glass fiber cable coatings; materials for holographic recording; magnetic recording materials; optical switches; plating masks; etching masks; screen printing stencils; touch panels such as transparent conductive films; MEMS elements; nanoimprint materials; photofabrication applications, such as two-dimensional and three-dimensional high-density mounting and the like of semiconductor packages; decoration sheets; artificial nails; glass-alternative optical films; electronic papers; optical disks; micro-lens arrays used in projectors, optical communication lasers and the like; prism lens sheets used in backlights of liquid crystal displays; Fresnel lens sheets used in the screens of projection televisions and the like; lens parts of lens sheets such as lenticular lens sheets; backlights and the like using such sheets; optical lenses, such as microlenses and image pickup lenses; optical elements; optical connectors; optical waveguides; insulation packings; heat-shrinkable rubber tubes; O-rings; sealing agents for display devices; protective materials; optical fiber protection materials; adhesives; die bonding agents; high-heat radiation materials; high-heat-resistant sealing materials; members for solar cells, fuel cells and secondary batteries; solid electrolytes for batteries; insulation coating materials; photosensitive drums for copying machines; gas separation membranes; civil engineering and construction materials, such as concrete protecting materials, linings, soil injection agents, sealing agents, cold-heat storage materials, glass coatings and foams; medical materials, such as tube/seal materials, coating materials, sealing materials for sterilizers, contact lenses, oxygen enrichment membranes, and biochips; automobile components; and various mechanical components.

EXAMPLES

The present invention will now be described in more detail by way of examples thereof; however, the present invention is not restricted thereto by any means.

Examples 1 to 5 and Comparative Example

Measurement of Acid Generation Temperature

The acid generation temperature was measured for Compound Nos. 4, 5, 20, 27 and 34 as Examples 1 to 5, respectively, as well as a comparative compound represented by the following chemical formula. The results thereof are shown in Table 1. It is noted here that the acid generation temperature was defined as the exothermic temperature that was determined by weighing 10 mg of each sample obtained by mixing 1.0 g of the epoxy compound shown below and 0.1 g of the respective compound, and subsequently measuring the TG/DTA (heating: 10° C./min, from 25° C. to 400° C.) thereof.

Comparative Compound

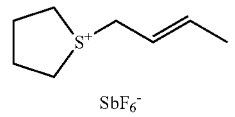

Epoxy Compound

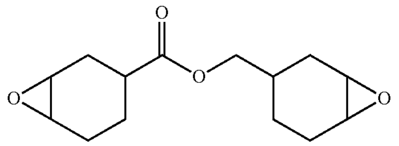 [SMILES: O=C(OCC1CCC2OC2C1)C1CCC2OC2C1]

| | | Acid generation temperature (° C.) |
|---|---|---|
| Example 1 | Compound No. 4 | 226 |
| Example 2 | Compound No. 5 | 216 |
| Example 3 | Compound No. 20 | 221 |
| Example 4 | Compound No. 27 | 209 |
| Example 5 | Compound No. 34 | 219 |
| Comparative Example | Comparative Compound | 134 |

As apparent from Table 1 above, the thermal acid generator of the present invention was confirmed to have a high acid generation temperature.

The invention claimed is:

1. A thermal acid generator selected from the group consisting of:

Compound No. 44

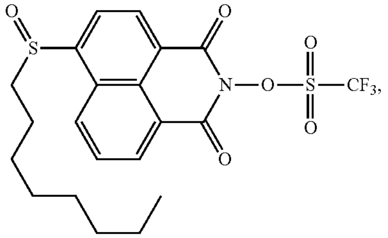

-continued

Compound No. 46

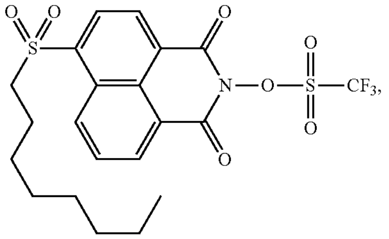

Compound No. 47

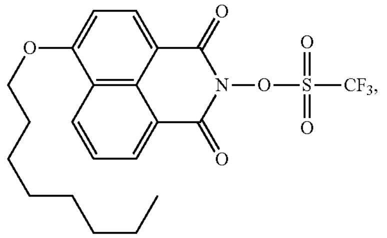

Compound No. 50

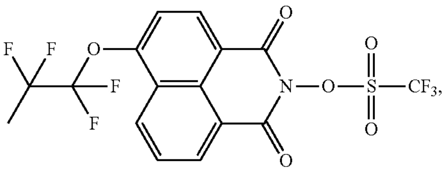

Compound No. 51

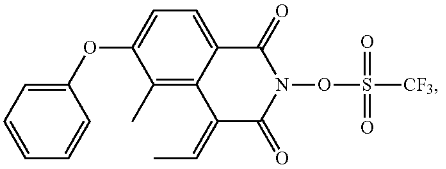

Compound No. 56

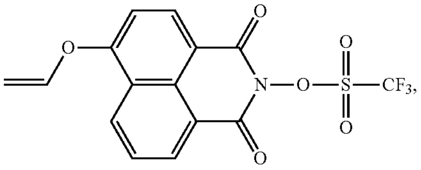

-continued

Compound No. 57

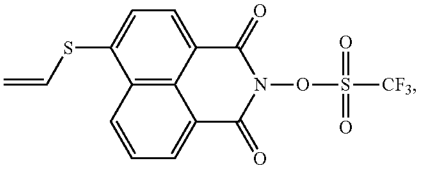

and

Compound No. 58

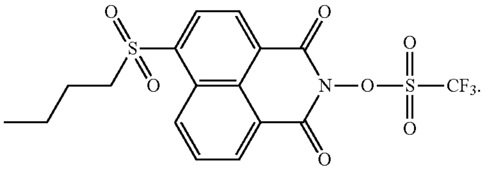

2. A resist composition comprising the thermal acid generator according to claim 1.

3. A method of making a resist, said method comprising:

heating an acid-reactive organic substance and the thermal acid generator of claim 1, wherein said heating of the thermal acid generator releases a Lewis acid to induce a polymerization or cross-linking of said acid-reactive organic substance to make said resist;

wherein the polymerization or cross-linking is performed at a heating condition of 200 to 250° C. for 1 to 100 minutes.

4. A resist obtained by the method according to claim 3.

5. A method of making a resist, said method comprising:

heating an acid-reactive organic substance and the thermal acid generator according to claim 1, wherein said heating of the thermal acid generator releases a Lewis acid to induce a polymerization or cross-linking of said acid-reactive organic substance to make said resist;

wherein the polymerization or cross-linking is performed at a heating condition of 70 to 300° C. for 1 to 100 minutes; and wherein an amount of the thermal acid generator is 0.05 to 100 parts by mass with respect to 100 parts by mass of the acid-reactive organic substance.

6. A resist obtained by the method according to claim 5.

* * * * *